United States Patent
Koo et al.

(10) Patent No.: US 8,192,942 B2
(45) Date of Patent: Jun. 5, 2012

(54) AFFINITY SEPARATION BY PARTITION ENHANCING MATERIAL CONJUGATED BIOMOLECULES IN AQUEOUS TWO-PHASE EXTRACTION SYSTEM

(75) Inventors: Yoon-Mo Koo, Seoul (KR); Woo-Jin Chang, Anyang-si (KR); Hye-Mee Park, Seoul (KR)

(73) Assignee: INHA-Industry Partnership Institute, Incheon (KR)

( * ) Notice: Subject to any disclaimer, the term of this patent is extended or adjusted under 35 U.S.C. 154(b) by 576 days.

(21) Appl. No.: 12/303,364

(22) PCT Filed: Jan. 21, 2008

(86) PCT No.: PCT/KR2008/000356
§ 371 (c)(1),
(2), (4) Date: Dec. 3, 2008

(87) PCT Pub. No.: WO2008/088200
PCT Pub. Date: Jul. 24, 2008

(65) Prior Publication Data
US 2009/0209735 A1    Aug. 20, 2009

(30) Foreign Application Priority Data
Jan. 19, 2007  (KR) ........................ 10-2007-0006001

(51) Int. Cl.
*G01N 33/53* (2006.01)
*G01N 33/535* (2006.01)
*G01N 33/536* (2006.01)
*C12Q 1/28* (2006.01)

(52) U.S. Cl. ............. 435/7.1; 435/7.9; 435/28; 436/536
(58) Field of Classification Search ........................ None
See application file for complete search history.

(56) References Cited

U.S. PATENT DOCUMENTS
6,437,101 B1    8/2002    Hayenga et al.

FOREIGN PATENT DOCUMENTS
KR    1019990086127    12/1999
KR    1020010108400    12/2001

OTHER PUBLICATIONS

Kim A. Sharp et al., Synthesis and Application of a Poly(ethylene glycol)-Antibody Affinity Ligand for Cell Separation in Aqueous Polymer Two-Phase Systems, Analytical Biochemistry,1986, 110-117, 154.
A. Kumar et al., Type-Specific Separation of Animal Cells in Aqueous Two-Phase Systems using Antibody Conjugates with Temperature-Sensitive Polymers, Biotechnology & Bioengineering, 2001, 570-580, 75.
M.S. Long et al., Nanoparticle Conjugation Increases Protein Partitioning in Aqueous Two-phase Systems, Analytical Chemistry, 2006, 379-86, 78(2).

*Primary Examiner* — Shafiqul Haq
(74) *Attorney, Agent, or Firm* — Lucas & Mercanti, LLP (57) ABSTRACT

The present invention relates to a method for separating a material that has affinity to an antibody by using a protein-antibody conjugate with modified partition characteristics, more precisely a method for affinity separation to separate a material specifically binds to an antibody, in which an antibody is conjugated to a protein to modify partition characteristics of the protein-antibody conjugate. The method of the present invention can be effectively and widely used as a safe and efficient separation method for biomolecules since it takes advantages of safe aqueous two-phase extraction system and high selective molecular specific conjugation.

5 Claims, 6 Drawing Sheets

**Affinity separation
in 10% PEG 1450 and 15% PPB system**

Fig. 8

**Affinity separation
in 5% PEG 8000 and 5% dextran T500 system**

AFFINITY SEPARATION BY PARTITION ENHANCING MATERIAL CONJUGATED BIOMOLECULES IN AQUEOUS TWO-PHASE EXTRACTION SYSTEM

CROSS-REFERENCE TO RELATED APPLICATIONS

This application is a 371 of PCT/KR2008/000356, filed on Jan. 21, 2008, which claims the benefit of Korean Patent Application No. 10-2007-0006001, filed on Jan. 19, 2007, the contents of each of which are incorporated herein by reference.

BACKGROUND OF THE INVENTION

1. Field of the Invention

The present invention relates to a method for separating a material that has affinity to an antibody moiety of a protein-antibody complex which has modified partition characteristics, more precisely an affinity separation method to separate a material specifically binds to an antibody moiety of the complex, in which a protein changes the partition characteristics of the protein-antibody complex.

2. Description of the Related Art

Separation of biomolecules is a very important, essential technique in the production of biological molecules including pharmaceutics, cell therapy industries, which are growing everyday. However, biomolecules are fragile comparing with chemical compounds, and have disadvantage of complicated purification process because of numbers of similar materials having similar physical and chemical characteristics in the solution. The separation of biomolecules via aqueous two-phase extraction system favors maintaining the stability of biomolecules, since this technique does not require an organic solvent, and makes the complicated purification process simple. Aqueous two-phase extraction system is composed of two different aqueous solutions containing high-molecular substances or high molecular substance and salt together at a required content, and at this time, two phases are formed in the system which are immiscible together because of electrostatic repulsion force between the substances.

The principal of the separation using aqueous two-phase extraction system is as follows; when high molecular weight substance such as polyethylene glycol and salt such as phosphate are mixed at a certain ratio, it is divided into two phases, the upper polyethylene glycol phase and the lower phosphate phase, owing to the difference of density and the molecular level repulsion between polyethylene glycol and salt. At this time, when the target materials for separation are added, these materials are crowded in one of the two phases according to their preference, resulted from the principle that each phase has different physical, chemical characteristics according to its components and compositions.

Mainly used polymer for composing aqueous two-phase extraction system is exemplified by polyethylene glycol, polyvinyl alcohol, dextran and oligosaccharide. The salt used for forming aqueous two-phase extraction system is exemplified by potassium phosphate, sodium phosphate, ammonium sulfate and magnesium sulfate. Aqueous two-phase extraction system contains water at least 65-80%, by which stability of biomolecules can be maintained. Such aqueous two-phase extraction system can be formed by various materials, which favors separation of biomolecules.

Up to date, it has been attempted in aqueous two-phase extraction system to change concentrations of materials forming the system and molecular weights of high molecular substances according to a target material for separation. In particular, various salts have been tried because salts affect partition characteristics significantly by changing surface properties of a target material or hydrophobicity of aqueous two-phase extraction system. However, the addition of salts increases osmotic pressure in solution, which might reduce stability of biomolecules and decreases selectivity because it affects not only the target material but also partition coefficients of other materials. So, it is very difficult to determine the optimum kind and concentration of such salt.

To overcome the above problem, it has been tried to use biological or chemical affinity in aqueous two-phase extraction system. The material used for enhancing affinity in aqueous two-phase extraction system is exemplified by antibodies, DNA, metal ions and surfactants.

In relation to this invention, there was an example of affinity separation using an antibody in aqueous two-phase extraction system, in which a temperature sensitive polymer was conjugated to an antibody as a ligand, to separate animal cells at a certain temperature (A. Kumar et al., Biotechnol. Bioeng., 75, 570-580, 2005). But, to increase separation efficiency, the temperature had to be maintained unchanged, otherwise biomolecules would be denatured. Besides, the toxicity of the polymer used as a ligand should be considered.

Another example of affinity separation is to use PEGylated molecules prepared by conjugating an antibody to PEG (polyethylene glycol) (Kim A. Sharp et al. Anal. Biochem. 154, 110-117, 1985). However, this method has disadvantage of high price of modified PEG and the success of PEGylation might be vulnerable according to the modified PEG and antibody types.

Thus, in order to separate a target material selectively from impurities without damaging stability of biomolecules, the present inventors choose protein and aqueous two-phase extraction system which are capable of distributing target materials on the opposite phase from the one where the antibodies are distributed. Then, the present inventors completed this invention by confirming that the target materials mixed in impurities can be recovered by re-distributing to opposite phase.

SUMMARY OF THE INVENTION

Accordingly, the present invention has been made keeping in mind the above problems occurring in the prior art, and an object of the present invention is to provide an affinity separation method in aqueous two phase extraction system using a protein as a ligand carrier effective in the affinity separation, which facilitates the safe and secured distribution of biomolecules in aqueous two-phase extraction system and has high antibody conjugation efficiency.

To achieve the above object, the present invention provides a method for separating a target material based on affinity comprising the following steps:

a) preparing a B-P conjugate by conjugating partition enhancing material (P) to affinity molecule (B) binding molecular specifically to target material (T) with modifying partition coefficient of B in order to locate the B-P conjugate in the opposite phase from where the target material is located;

b) loading the conjugate prepared in step a) into aqueous two-phase extraction system composed of aqueous solution of water-soluble polymer containing T and aqueous solution of salt, and c) separating the T-B-P conjugate generated in step b).

The present invention provides a method for affinity separation in aqueous two-phase extraction system using an HRP-conjugated antibody. In this invention, the antibody-HRP conjugate facilitates separation of target material via antigen-antibody reaction using high efficient antibody-HRP conjugation. Therefore, the method of the present invention can be widely used for safe and effective separation of materials in aqueous two-phase extraction system.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Below, a detailed description will be given of the present invention.

Terms used in this invention are defined as follows.

Aqueous two-phase extraction system indicates the system forming two phases unmixed by electrostatic repulsion force among the materials, which is composed of two aqueous solutions containing polymers or polymer and salt together at a certain concentration.

Target material (T, target) indicates the material to be separated.

Partition enhancing material (P, partition) indicates the material capable of changing partition coefficient of affinity molecule by being conjugated to the affinity molecule binding to the target material in order for the target material and the affinity molecule to be located in different phases from each other.

Hereinafter, the present invention is described in detail.

The present invention provides a method for separating a target material based on affinity comprising the following steps:

a) preparing a B-P conjugate by conjugating partition enhancing material (P) to affinity molecule (B) binding molecular specifically to target material (T) with modifying partition coefficient of B in order to locate the B-P conjugate in the opposite phase from where the target material is located;

b) loading the conjugate prepared in step a) into aqueous two-phase extraction system composed of aqueous solution of water-soluble polymer containing T and aqueous solution of salt; and c) separating the T-P-P conjugate generated in step b).

The present inventors screened a conjugation protein capable of changing the partition coefficient of an antibody during affinity separation using the antibody in aqueous two-phase extraction system. As a result, when HRP (horseradish peroxidase) was used as a conjugation protein, the conjugation efficiency was proved to be high, and the commercialized HRP antibody conjugate could be easily obtained. For separation, partition coefficient (K, concentration of the material existing in the upper phase/concentration of the material existing in lower phase) has to be different. Considering the case that the HRP-conjugated antibody has the same partition coefficient with the not conjugated antibody, the present inventors examined whether or not these two antibodies had different partition coefficients in various aqueous two-phase extraction systems.

Figure 1:
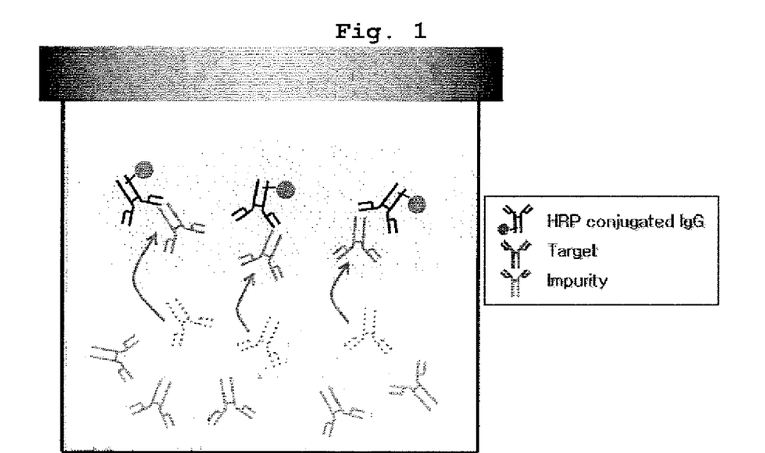
FIG. 1 is a diagram illustrating the affinity separation in aqueous two-phase extraction system using a protein-antibody conjugate.
Figure 2:
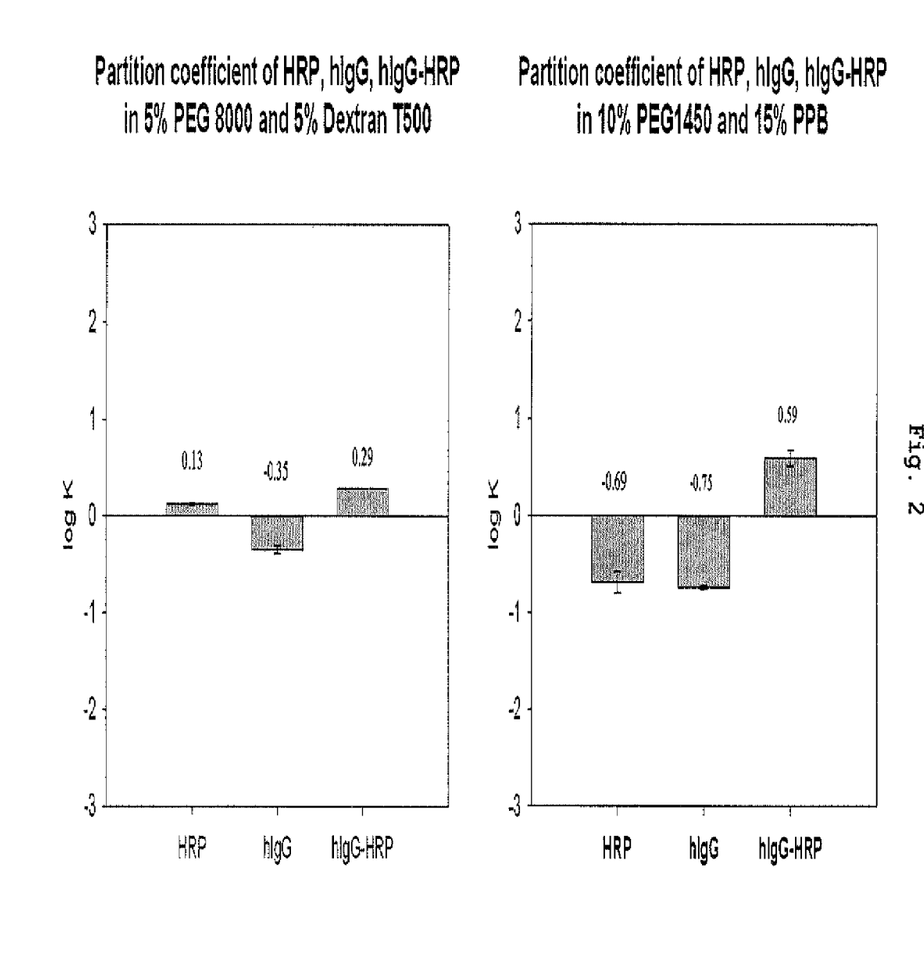
FIG. 2 is a set of graphs illustrating the difference of partition coefficients of HRP, hIgG, and hIgG-HRP in aqueous two-phase extraction system composed of PEG (molecular weight: 1450, 10%, w/w) and potassium phosphate solution (15%, w/w), or composed of PEC (molecular weight: 8000, 5%, w/w) and dextran T500 (molecular weight: 5000,000, 5%, w/w).

Particularly, to separate rabbit-anti human IgG, a target protein, human IgG (hIgG) and human IgG-HRP conjugate (hIgG-HRP) were selected for HRP and HRP-antibody conjugate respectively and aqueous two-phase extraction system was composed of PEG (molecular weight: 1450, 10%, w/w) and potassium phosphate solution (15%, w/w) or PEG (molecular weight: 8,000, 5%, w/w) and dextran T500 (molecular weight: 500,000, 5%, w/w). Partition coefficient of each HRP, hIgG and hIgG-HRP when they existed alone in each aqueous two-phase extraction system was investigated. As a result, hIgG-HRP had a preference for the upper phase more than HRP and hIgG did (see FIG. 2).

The present inventors also investigated partition tendency according to the molar ratio of a target protein to the HRP conjugated antibody in aqueous two-phase extraction system. Based on the partition tendency, the present inventors determined the favored conditions for separation of a target protein (kinds and concentrations of constituents of aqueous two-phase extraction system, molar ratio of a target protein to the antibody-HRP conjugate, etc).

As a result, optimum molar ratio of hIgG-HRP:rabbit anti-human IgG:goat anti-mouse IgG was 3:1:1 in the aqueous two-phase extraction system comprising PEG and potassium phosphate buffer, and 1:1:1 in the aqueous two-phase extraction system comprising PEG and dextran.

In this invention, a target material was located in the lower phase of aqueous two-phase extraction system along with impurities which were other antibodies. The present inventors induced the target protein to the upper phase of aqueous two-phase extraction system by using affinity binding between two materials via the antibody-HRP conjugate that had a preference for the upper phase and then isolated the upper phase to separate the target material and impurities.

In this method of the present invention, the target material is selected from the group consisting of cells, proteins, nucleic acid molecules, polysaccharides, glycoproteins, glycolipids and lipoproteins, but not always limited thereto.

In this method of the present invention, the molecular specific material can be any material operable as a ligand and an acceptor such as antibodies, antigens, enzymes and substrates, peptides, nucleotides, aptamers, dyes and metal ions. The partition enhancing material can be any polypeptide and peptide including HRP (horseradish peroxidase), alkaline phosphatase, beta-galactosidase, lysozyme and bovine serum albumin.

The polymer of step c) is preferably selected from the group consisting of PEG (polyethylene glycol), dextran, polyvinyl alcohol, polyethylene polypropylene block copolymer and oligosaccharide, but not always limited thereto.

The salt of step c) is preferably selected from the group consisting of potassium phosphate, sodium phosphate, ammonium sulfate and magnesium sulfate, but not always limited thereto.

In addition, the constituents of the aqueous two-phase extraction system composed of the aqueous solution of water-soluble polymer and the aqueous solution of salt can be selected from the group consisting of polyvinyl alcohol, dextran, polyethylene polypropylene block copolymer, oligosaccharide, potassium phosphate, sodium phosphate, ammonium sulfate and magnesium sulfate, in addition to PEG (polyethylene glycol) and potassium phosphate or PEG and dextran.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Partition Coefficient of Each Antibody-HRP Conjugate, Target Protein and Impurity The antibody-HRP conjugate, target protein and impurity of the present invention are respectively HRP (horseradish peroxidase)-conjugated IgG (hIgG-HRP), rabbit-anti human IgG having affinity to the conjugate, and goat anti-mouse IgG having no affinity to the conjugate (all purchased from Pierce Biotechnology, Inc., USA).

The aqueous two-phase extraction system used in this invention was composed of PEG (molecular weight: 1,450, 10%, w/w) and potassium phosphate buffer (15%, w/w) or PEG (molecular weight: 8,000, 5%, w/w) and dextran T500 (molecular weight: 500,000, 5%, w/w), in which hIgG-HRP had a preference for the upper phase (log K>0) and rabbit anti-human IgG and goat anti-mouse IgG had a preference for the lower phase (log K<0) (Table 1).

To compose the aqueous two-phase extraction system, 4 mother solutions concentrated double the concentration of the final concentration (PEG solution (molecular weight: 1,450, 20%, w/w), potassium phosphate buffer (30%, w/w), PEG solution (molecular weight: 8,000, 10%, w/w), dextran T500 solution (molecular weight: 500,000, 10%, w/w)) were first prepared. The PEG solution (molecular weight: 1,450) and the potassium phosphate solution or the PEG solution (molecular weight: 8,000) and the dextran solution were mixed by 0.5 g each to prepare aqueous two-phase extraction system solutions of 1 g in total weight (PEG (molecular weight: 1,450, 10%, w/w) and potassium phosphate buffer (15%, w/w) or PEG (molecular weight: 8,000, 5%, w/w) and dextran T500 (molecular weight: 500,000, 5%, w/w)). After mixing the mother solutions, centrifugation was performed at 3000 rpm for 15 minutes, which stood at room temperature for 1 hour to stabilize the phases.

Table 1: Partition coefficients of hIgG-HRP, rabbit anti-human IgG, and goat anti-mouse IgG in aqueous two-phase extraction system

TABLE 1

| Aqueous two-phase extraction system | Partition coefficient (log K) | | |
|---|---|---|---|
| | hIgG-HRP | Rabbit anti-human IgG | Goat anti-mouse IgG |
| PEG (MW 1450, 10%, w/w) and potassium phosphate solution (15%, w/w) | 0.59 | −0.34 | −0.68 |
| PEG (MW 8000, 5%, w/w) and dextran T500 (MW 500000, 5%, w/w) | 0.29 | −0.04 | −0.70 |

EXAMPLE 2

Changes of Partition Coefficient Over Molar Ratios of hIgG-HRP to Rabbit Anti-Human IgG, and hIgG-HRP to Goat Anti-Mouse IgG As explained in Example 1, hIgG-HRP, rabbit anti-human IgG and goat anti-mouse IgG had a preference for different phases. In this example, the present inventors investigated how the molar ratio of hIgG-HRP to rabbit anti-human IgG and the molar ratio of hIgG-HRP to goat anti-mouse IgG could affect partition coefficients of them.

Figure 3:
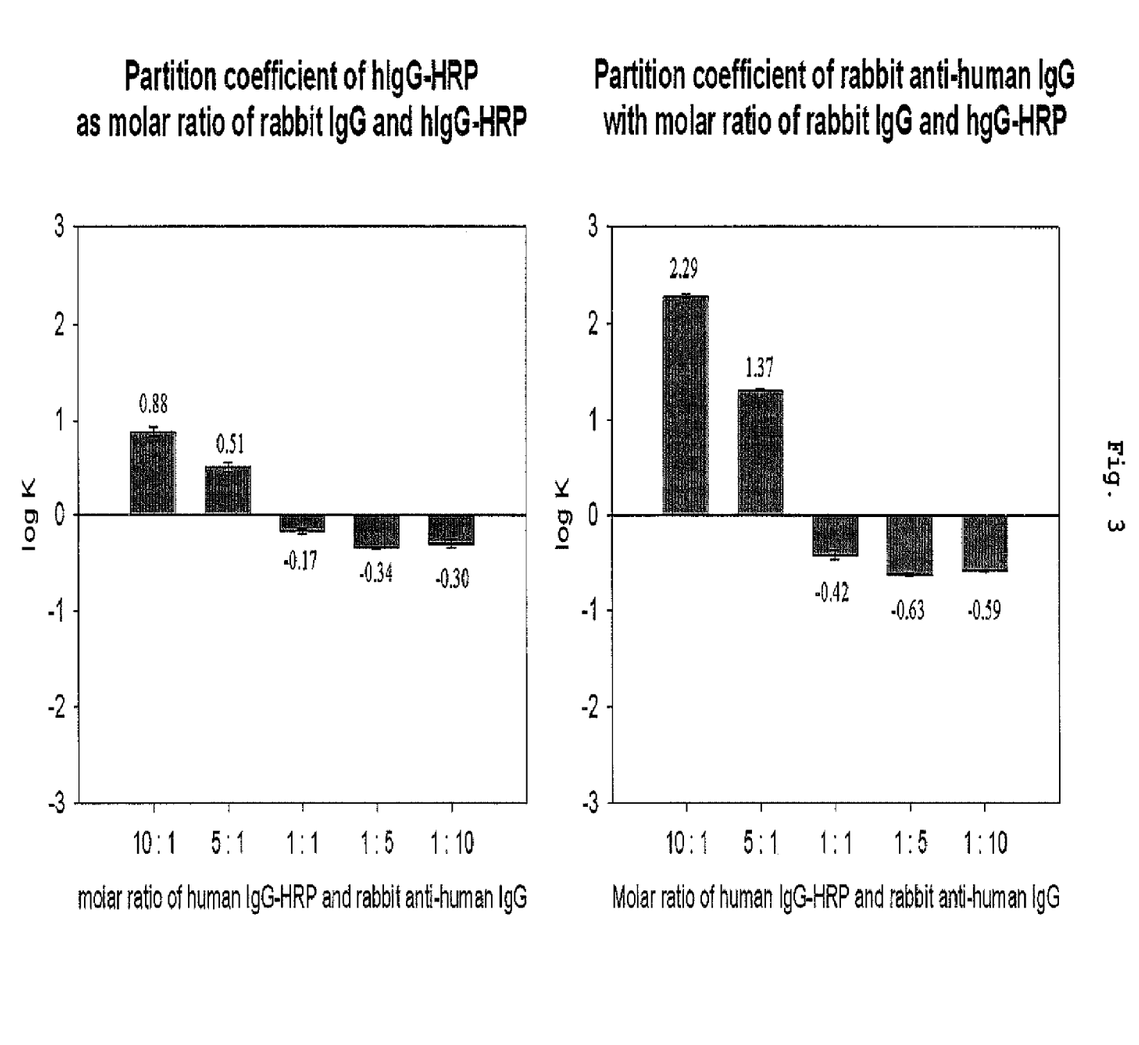
FIG. 3 is a set of graphs illustrating the changes in each partition coefficient over molar ratio of hIgG-HRP having affinity to rabbit anti-human IgG in PEG (molecular weight: 1450, 10%, w/w) and potassium phosphate solution (15%, w/w).
Figure 4:
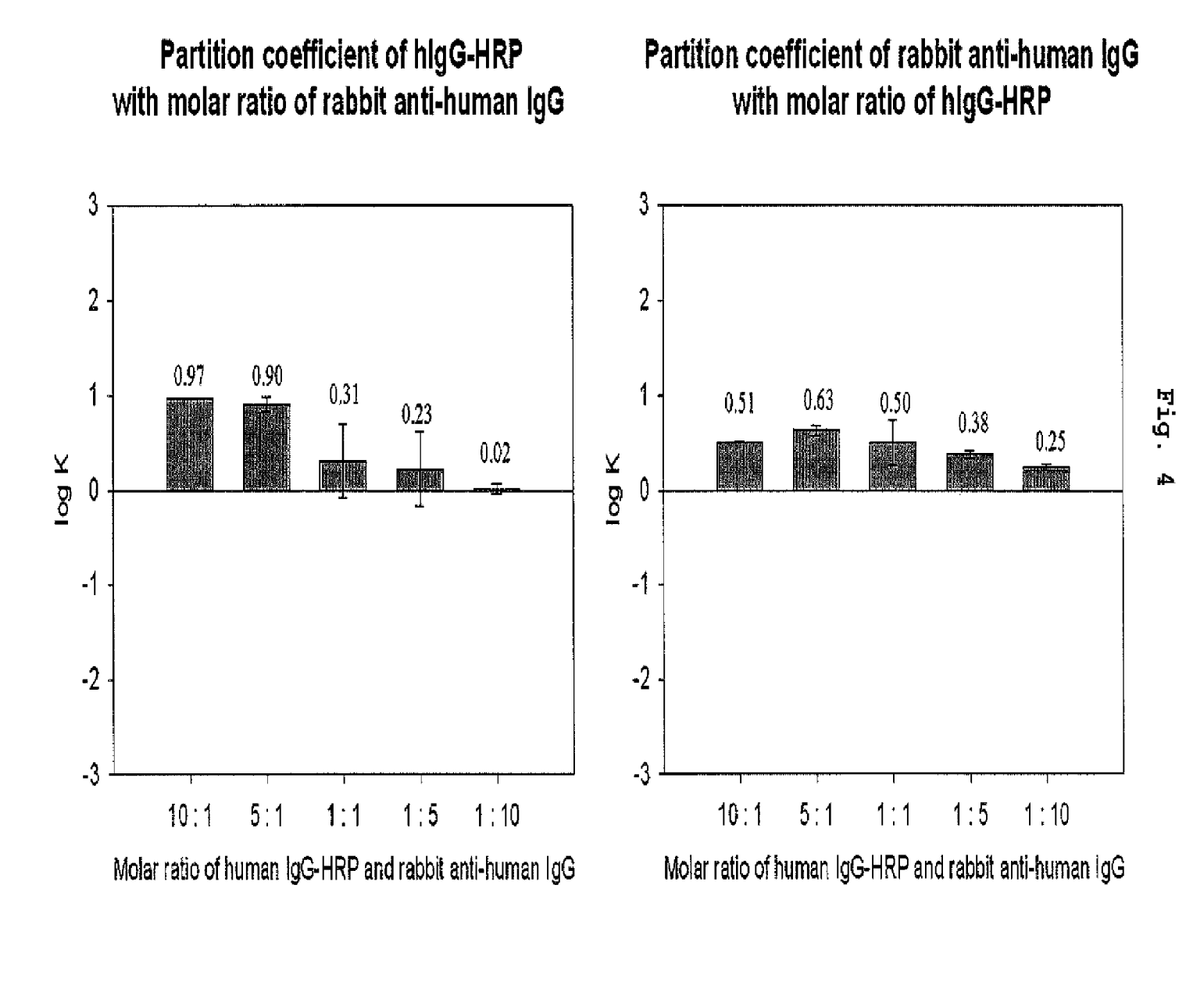
FIG. 4 is a set of graphs illustrating the changes of each partition coefficient over molar ratio of hIgG-HRP having affinity to rabbit anti-human IgG in PEG (molecular weight: 8,000, 5%, w/w) and dextran T500 (molecular weight: 500,000, 5%, w/w).

<2-1> Changes of Affinity Partition Coefficient According to Molar Ratio of hIgG-HRP to Rabbit Anti-Human IgG In aqueous two-phase extraction system composed of PEG (molecular weight: 1,450, 10%, w/w) and potassium phosphate buffer (15%, w/w) or PEG (molecular weight: 8,000, 5%, w/w) and dextran T500 (molecular weight: 500,000, 5%, w/w), the molar ratio of hIgG-HRP to anti-human IgG was changed. As a result, as the molar ratio of hIgG-HRP increased, partition coefficient of rabbit anti-human IgG having affinity to the hIgG-HRP increased. On the contrary, as the molar ratio of rabbit anti-human IgG increased, partition coefficient of hIgG-HRP decreased (FIGS. 3 and 4). From the results, it was confirmed that the affinity separation of target materials using the antibody-HRP conjugate was successful and in particular the molar ratio of the two materials affected the separation efficiency.

The present inventors also confirmed that the optimum molar ratios of hIgG-HRP:rabbit anti-human IgG:goat anti-mouse IgG was 3:1:1 in salt-based aqueous two-phase extraction system and 1:1:1 in dextran-based aqueous two-phase extraction system.

Figure 5:
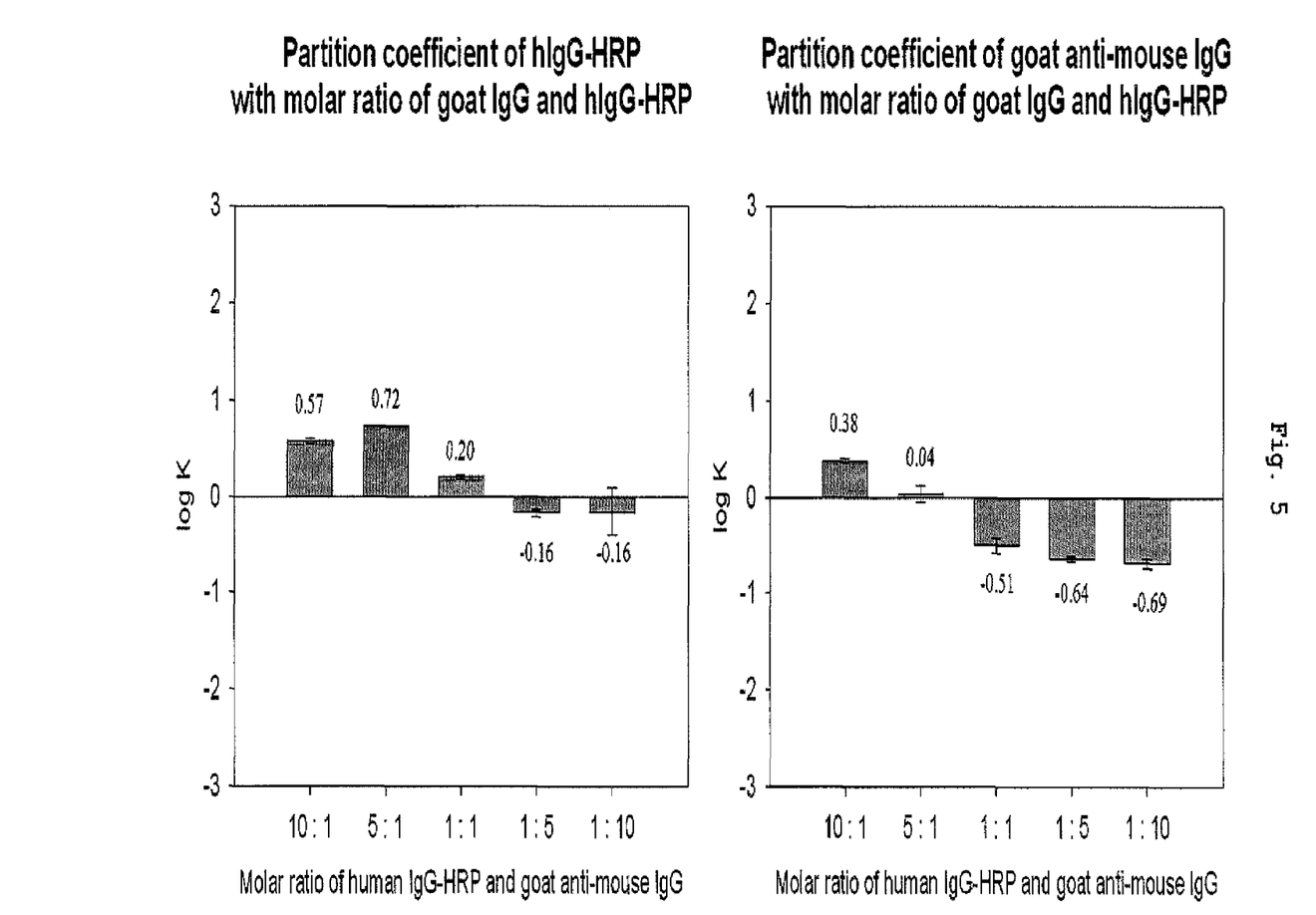
FIG. 5 is a set of graphs illustrating the changes of each partition coefficient over molar ratio of hIgG-HRP without affinity to goat anti-mouse IgG in PEG (molecular weight: 1450, 10%, w/w) and potassium phosphate solution (15%, w/w).
Figure 6:
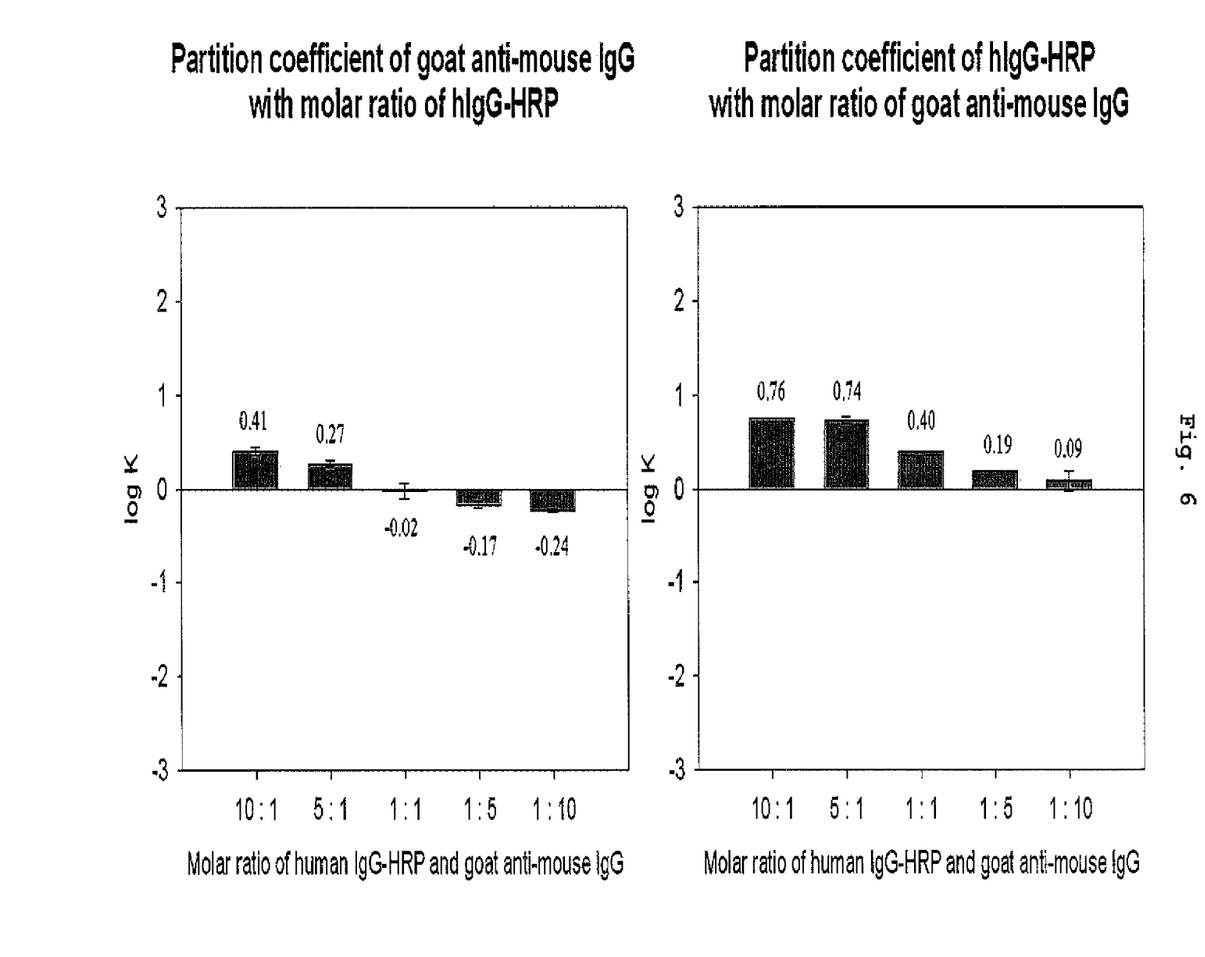
FIG. 6 is a set of graphs illustrating the changes of each partition coefficient over molar ratio of hIgG-HRP without affinity to goat anti-mouse IgG in PEG (molecular weight: 8000, 5%, w/w) and dextran T500 (molecular weight: 500,000, 5%, w/w).

<2-2> Changes of Non-Affinity Partition Coefficient According to Molar Ratio of hIgG-HRP to Goat Anti-Mouse IgG Experiment was performed with different molar ratios of hIgG-HRP to goat anti-mouse IgG in two different aqueous two-phase extraction systems composed of PEG (molecular weight: 1,450, 10%, w/w) and potassium phosphate solution (15%, w/w) or PEG (molecular weight: 8,000, 5%, w/w) and dextran T500 (10:1, 5:1, 1:1, 1:5, 1:10). As a result, as the molar ratio of hIgG-HRP increased, partition coefficient of goat anti-mouse IgG having no affinity to the hIgG-HRP increased to some degree. On the contrary, as the molar ratio of goat anti-mouse IgG increased, partition coefficient of hIgG-HRP decreased to some degree (FIGS. 5 and 6).

The above results resulted from cross-reactivity between goat anti-mouse IgG and hIgG-HRP. It was expected at the beginning that the material without affinity would not have preference for the upper phase in aqueous two-phase extraction system even with the reaction with hIgG-HRP. However, non-specific affinity between the two materials was in fact found and that made the different result from what expected. This affinity will be weaker than that when the rabbit anti-human IgG is included in the solution together, and affinity binding is competitive. Thus, such non-specific conjugation would not affect much the affinity separation.

EXAMPLE 3

Affinity Separation Using Affinity Partition in Aqueous Two-Phase Extraction System It is the last object of the present invention to separate rabbit anti-human IgG with high efficiency and purity by arranging partition of the target material, rabbit anti-human IgG, in the upper phase using hIgG-HRP. The following experiments were performed to measure the purity and partition coefficient of rabbit anti-human IgG at the molar ratio determined in the above.

<3-1> Affinity Separation in PEG (Molecular Weight: 1,450, 10%, w/w) and Potassium Phosphate Solution (15%, w/w)

Figure 7:
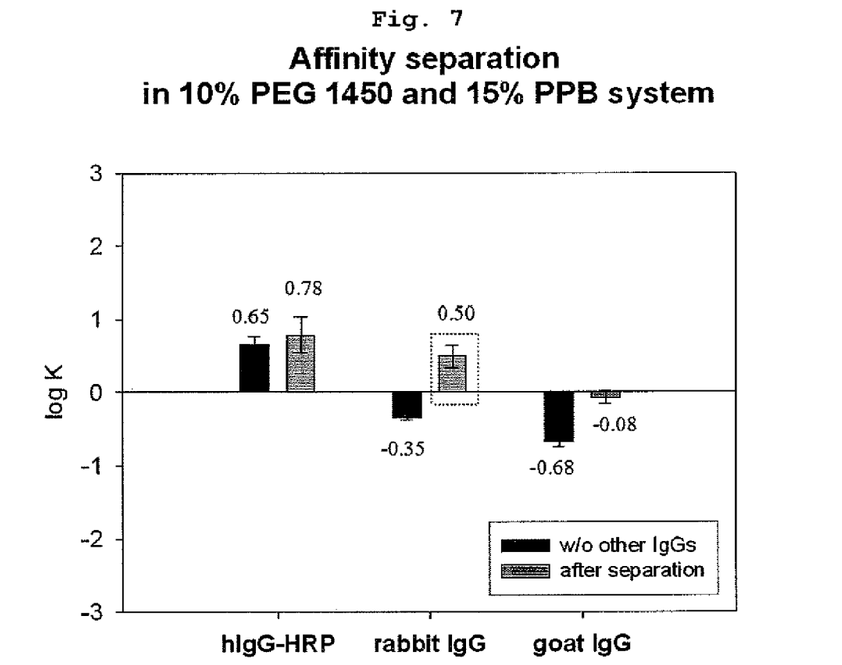
FIG. 7 is a graph illustrating the affinity separation in PEG (molecular weight: 1450, 10%, w/w) and potassium phosphate solution (15%, w/w).

Based on the results of Examples <2-1> and <2-2>, the molar ratio of hIgG-HRP:rabbit anti-human IgG:goat anti-mouse IgG to arrange rabbit anti-human IgG in the upper phase was determined to be 3:1:1. At that molar ratio, affinity separation was performed. As a result, partition coefficient of rabbit anti-human IgG was significantly increased from −0.35 to 0.50 by hIgG-HRP, indicating that the target material moved to the upper phase and distributed mostly in the upper phase. In the meantime, partition coefficient of goat anti-mouse IgG was a little increased from −0.68 to −0.08, but still mainly existed in the lower phase (FIG. 7). The purity of rabbit anti-human IgG existed in the upper phase was 72.37%, suggesting that affinity separation of the rabbit anti-human IgG could be successfully induced. The purity was calculated by dividing the amount of rabbit anti-human IgG existed in the upper phase by the sum of the amounts of hIgG-HRP, rabbit anti-human IgG, and goat anti-mouse IgG existed in the upper phase, which was multiplied by 100.

<3-1> Affinity Separation in PEG (Molecular Weight: 8,000, 5%, w/w) and Dextran (Molecular Weight: 500,000, 5%, w/w)

Figure 8:
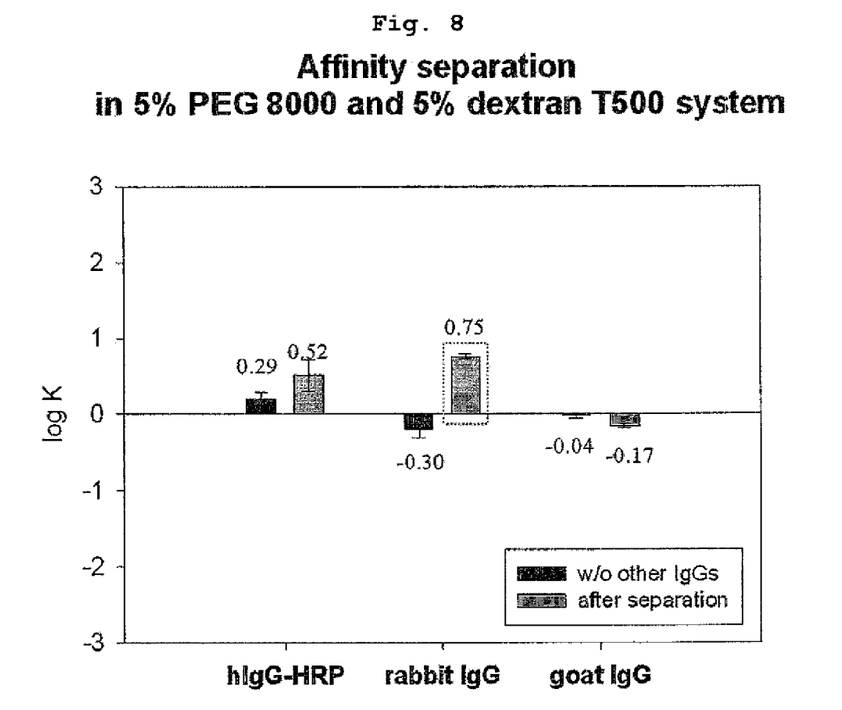
FIG. 8 is a graph illustrating the affinity separation in PEG (molecular weight: 8,000, 5%, w/w) and dextran T500 (molecular weight: 500,000, 5%, w/w).

Based on the results of Examples <2-1> and <2-2>, the molar ratio of hIgG-HRP:rabbit anti-human IgG:goat anti-mouse IgG, to arrange rabbit anti-human IgG in the upper phase was determined to be 1:1:1. As a result, partition coefficient of rabbit anti-human IgG was increased from −0.30 to 0.75, while partition coefficient of goat anti-mouse IgG was reduced from −0.04 to −0.17, indicating that the goat anti-mouse IgG was rather distributed in the lower phase (FIG. 8). The purity of rabbit anti-human IgG distributed in the upper phase was 87.68%.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for separating a target material (T) based on an aqueous two phase extraction system comprising the following steps:
   a) preparing a B-P conjugate by conjugating a partition enhancing material (P) to an affinity molecule (B), wherein the affinity molecule is an antibody that specifically binds the target material (T) thereby modifying the partition coefficient of B in order to locate the B-P conjugate in the opposite phase from where the target material is located;
   b) loading the B-P conjugate prepared in step a) into an aqueous two-phase extraction system that contains the target material (T), wherein the aqueous solution two-phase extraction system comprises a salt and a water-soluble polymer at a certain concentration, thereby generating a T-B-P conjugate by binding B-P conjugate to the target material (T), which is distributed mostly to upper water-soluble polymer phase; and
   c) isolating the upper water-soluble polymer phase to separate the T-B-P conjugate thereby separating the target material,
   wherein
   the partition enhancing material is HRP (horseradish peroxidase); and
   the water-soluble polymer is selected from the group consisting of PEG (polyethylene glycol) and dextran.

2. The method for separating a target material according to claim 1, wherein the target material is selected from the group consisting of cell, protein, nucleic acid molecule, polysaccharide, glycoprotein, glycolipid and lipoprotein.

3. The method for separating a target material according to claim 2, wherein the protein is selected from the group consisting of peptide ligand, enzyme and antibody.

4. The method for separating a target material according to claim 1, wherein the salt is selected from the group consisting of potassium phosphate, sodium phosphate, ammonium sulfate and magnesium sulfate.

5. The method for separating a target material according to claim 1, wherein the target material is anti-human IgG and the affinity molecule is human IgG.

\* \* \* \* \*